United States Patent
Nohta et al.

[11] Patent Number: 5,824,559
[45] Date of Patent: Oct. 20, 1998

[54] METHOD OF ANALYZING 5-HYDROXYINDOLES AND CATECHOLAMINES, AND A DEVICE FOR PERFORMING THE SAME

[75] Inventors: Hitoshi Nohta, Hamakita; Masatoshi Yamaguchi, Fukuoka; Junichi Ishida, Fukuoka; Kiyoshi Zaitsu, Fukuoka; Hiroko Iida, Fukuoka, all of Japan

[73] Assignee: Laboratory of Molecular Biophotonics, Hamakita, Japan

[21] Appl. No.: 664,909

[22] Filed: Jun. 17, 1996

[30] Foreign Application Priority Data

Jun. 15, 1995 [JP] Japan .................... 7-149126
Jun. 22, 1995 [JP] Japan .................... 7-156164
Jun. 22, 1995 [JP] Japan .................... 7-156177

[51] Int. Cl.$^6$ .................... G01N 33/48; G01N 21/76; G01N 30/02
[52] U.S. Cl. .................... 436/111; 436/63; 436/89; 436/91; 436/96; 436/106; 436/131; 436/161; 436/164; 436/166; 436/172; 436/174; 422/52; 422/69; 422/70; 422/81; 422/82.05
[58] Field of Search .................... 436/63, 89, 91, 436/96, 106, 111, 131, 161, 164, 166, 172, 174; 422/52, 69, 70, 81, 82.05

[56] References Cited

U.S. PATENT DOCUMENTS

| | | | |
|---|---|---|---|
| 4,181,650 | 1/1980 | Maier, Jr. | .................... 436/15 X |
| 4,419,452 | 12/1983 | Imai et al. | .................... 436/96 X |
| 4,834,918 | 5/1989 | Wulff et al. | |

FOREIGN PATENT DOCUMENTS

| | | |
|---|---|---|
| 0242245 | 10/1987 | European Pat. Off. . |
| 2728193 | 2/1979 | Germany . |
| 3545398 | 6/1987 | Germany . |
| 2026159 | 1/1980 | United Kingdom . |
| 1578275 | 11/1980 | United Kingdom . |
| 2095830 | 10/1982 | United Kingdom . |
| 2278442 | 11/1994 | United Kingdom . |

OTHER PUBLICATIONS

Y. Umegae et al. *Anal. Chim. Acta* 1988, 208, 59–68.
Y. Umegae et al, *Chem. Pharm. Bull.* 1990, 38, 2293–2285.
J. Ishida et al, *Analyst* 1991, 116, 301–307.
H. Nohta et al. *Anal. Chim. Acta* 1992, 267, 137–139.
S. Higashidate et al. *Analyst.* 1992, 117, 1863–1868.
H. Nohta et al. *Anal. Sci.* 1994, 10, 5–9.
Z. Pang et al. *Fenxi Kexue Xuebao* 1994, 10, 53–58.
G.H. Ragab et al. *Anal. Chim. Acta* 1994, 298, 431–438.
Analyst, Mar. 1991, vol. 116, Spectrofluorimetric Determination of 5–Hydroxyindoles With Benzylamine or 3,4–Dimetoxybenzylamine as a Selective Fluorogenic Reagent,J.Ishida et al. pp. 301–304.

(List continued on next page.)

*Primary Examiner*—Arlen Soderquist
*Attorney, Agent, or Firm*—Cushman Darby & Cushman IP Group of Pillsbury Madison & Sutro LLP

[57] ABSTRACT

A method and a device for the analysis of 5-hydroxyindoles or catecholamines with high sensitivity. New chemiluminescence labeling agents, 6-aminomethylphthalhydrazide or 1,2-bis(phthalhydrazino)ethylenediamine, are reacted with 5-hydroxyindoles or catecholamines to form their stable derivatives. The derivatives emit strong luminescence in the presence of an oxidizing agent. In the chemiluminescence detection method, there is extremely low background noise and thus the method enables analysis with high sensitivity. The analysis of 5-hydroxyindoles or catecholamines in a sample is enabled by a method (1), in which each of the above-mentioned components is separated, reacted with said chemiluminescence labeling agent to form its derivative, and then chemiluminescent emitted by the reaction of the derivative with an oxidizing agent is detected, or by another method (2), in which the mixture of 5-hydroxyindoles or catecholamines in a sample is reacted with the chemiluminescence labeling agent to form its derivative mixture, subsequently each derivative is separated, and then chemiluminescent emitted by the reaction of the derivative with an oxidizing agent is detected.

13 Claims, 5 Drawing Sheets

OTHER PUBLICATIONS

Analytica Chimica Acta 208 (1988) 59–68, 1,2–Diarylethylenediamines as Fluorogenic Reagents for Catecholamines, Yoshihiko Umegae et al. pp. 59–68.

Patent Abstracts of Japan 56–133649 (A), vol. 6, No. 8, Jan. 19, 1982.

Patent Abstracts of Japan 62–190446 (A), vol. 12, No. 43, Feb. 9, 1988.

Biochemische Analytik, "Angewandte Chemilumineszenz", Nachr. Chem. Tech. Lab. 40 (1992) Nr. 5, pp. 547–553.

METHOD OF ANALYZING 5-HYDROXYINDOLES AND CATECHOLAMINES, AND A DEVICE FOR PERFORMING THE SAME

BACKGROUND OF THE INVENTION

1. Field of the Invention

This invention relates to a chemiluminescence labeling agent for analysis of 5-hydroxyindole and its analog ("5-hydroxyindoles") and/or catecholamine and its analog ("catecholamines") in a sample, to a method for the measurement of them using the above-mentioned labeling agent, and to a device for the measurement of them.

2. Related Background Art 5-hydroxyindoles is a generic term referred to those which have an indole structure with a hydroxy group at 5-position, and is known to be produced in the biosynthesis and the metabolic pathway of bioactive substances of serotonin or melatonin in vivo, using a tryptophan as a starting material. Among those, serotonin exists in a nerve cell, an Enterochromaffin cell and a platelet and the like as a neurotransmitter or a smooth muscle contraction substance, and takes part in various regulatory mechanisms of life phenomena. Also, 5-hydroxyindole acetic acid is the final metabolite of 5-hydroxyindole compounds, and it is an essential one in biochemical and pharmacological study of a endocrine system and a nerve system and the like, and in clinical chemical study of wide range of diseases because of its proper reflection of the secretion of tryptophan or serotonin in the body.

Conventional analytical methods for 5-hydroxyindoles include Radioimmunoassay, gas chromatography-mass spectrometry (GC-MS) method, high performance liquid chromatography (HPLC) method and the like. The radioimmunoassay method provide handy and high sensitivity analysis, but has also limitation due to equipments handling, radioisotopes discarding and the like. Further there is another problem about its analytical specificity, because many analogous compounds in a biosample may cause a cross reaction. A GC-MS method has high specificity, but it has a problem that it needs complicated steps for formation of volatile derivatives from compounds to be analyzed. HPLC method is one of the most frequently used at present, and a fluorescence detection of naturally occuring fluorescence of the compounds to be analyzed, and the electrochemical detection are known as a detection method therefor. The fluorescence detection has a problem of increased background noise owing to the appearance of many of hindrance peaks derived from an aromatic amino acid and various types of indole. On the other hand, the electrochemical detection has also a problem of increased background noise owing to the coexistence of many of hindrance peaks derived from reduced materials of catechols, 4-hydroxy-3-methoxyphenyl compounds, indoles or the others. Thus, those problems require special separation method including a complicated pretreatment or column switching to obtain high sensitivity analysis in a biosample.

A luminescence detection method is similar to the above-mentioned fluorescence method in general. However, a chemiluminescence detection method, in which the luminescence is based on the chemical reaction, and consequently observes only luminescence based on the chemical reaction of a compounds to be analyzed. Because of no need of excitation light, its background noise should be extremely low to provide an analysis with high sensitivities.

Catecholamines is a general term referred to a bioamine which has 3,4-dihydroxyphenyl structure and in particularly, norepinephrine, epinephrine and dopamine serve important roles in the maintenance of constancy in an organism as a adrenocortical hormone or a neurotransmitter. Thus, the analysis of catecholamines is also essential one in biochemical, pharmacological and clinical chemical study of a endocrine system and a nerve system and the like. Such conventional analysis methods or analysis devices for catecholamines in a biosample, such as blood plasma and urine, generally separate the sample to each component by using a high-performance liquid chromatography, and quantify each separated catecholamines by using various detection methods. Such detection methods are known to be an electrochemical detection method, a fluorescence method (a natural fluorescence method and a fluorescence derivativation method) or other chemiluminescence methods and the like. Among those, an electrochemical detection method has the highest sensitivity, but it has a problem that it is difficult to detect extremely low concentration of catecholamines such as in plasma sample because of its weak selectivity of catecholamines. Although a method in which natural fluorescence is detected are simple among those fluorescence methods, generally its sensitivity is insufficient. Furthermore, a fluorescence derivativation method includes a method which uses ethylenediamine (ED method), a method which uses trihydroxyindole (THI method), and a method which uses 1,2-diphenylethylenediamine. Among those, ED method has a problem of its weak sensitivity. As for THI method, although it has advantageously high selectivity and sensitivity, it has a problem of its low detection sensitivity of dopamine. The method which uses 1,2-diphenyl ethylenediamine is known to have sensitivity equal to that of the electrochemical detection method and high selectivity. However, there is a problem that since the above-mentioned fluorescent methods generally require the irradiation using excitation light, fluorescence derived from impurities and the others except the material to be detected can not be avoid; thus fluorescent noise increases and prevents high sensitivity.

In contrast, although luminescence detection method is similar to the above-mentioned fluorescence method, it detects only luminescence due to a chemical reaction with catecholamine derivatives and not a luminescence induced by excitation light, and thus its background noise should be extremely low to provide an analytical method with high sensitivity.

SUMMARY OF THE INVENTION

To quantify extremely small amount of 5-hydroxyindoles in a biosample, particularly in plasma, by using HPLC method, at least about 0.5 ml of sample is conventionally required. It is desired, therefore, to develop a method with high sensitivity in which it can measure with only 100 μl or less of plasma. Accordingly, to satisfy the demand, it is needed to develop a chemiluminescence method in which there should be extremely low background luminescent noise. In other words, it is desired (1) to develop a reaction system which specifically and quantitatively react with 5-hydroxyindoles to form stable derivatives, and furthermore (2) to develop a reaction system which specifically and quantitatively react with that derivative so as to lead chemiluminescence.

Also, as for catecholamines; in the case of fluorescence method, at least 0.5 ml of sample is required to quantify extremely small amount of catecholamines in a biosample, particularly in plasma, even by using the above-mentioned 1,2-diphenylethylenediamine method which is considered to have the highest sensitivity. It is desired, therefore, to develop a method with high sensitivity in which it needs only 100 μl or less of plasma. To satisfy above demand, it is desired to develop a chemiluminescence method in which there should be extremely low background luminescent noise. In other words, it is desired (1) to develop a reaction system which specifically and quantitatively react with catecholamines to form a stable derivative, and furthermore (2) to develop a reaction system which specifically and quantitatively react with the derivative so as to lead chemiluminescence.

The inventors of the invention, as a result that they have researched devotedly to establish the above-mentioned purpose, have found out that 6-aminomethylphthalhydrazide or 1,2-bis(phthalhydrazino)ethylenediamine which has a dimer structure thereof, as new chemiluminescence labeling agents, can react with 5-hydroxyindoles and catecholamines to form their stable derivatives which have the similar characteristic structure, respectively, and furthermore that the above-mentioned derivatives emit strong luminescence in the presence of a proper oxidizing agent, and thus have completed the present invention.

Namely, as shown in FIG. 1 5-hydroxyindoles approximately quantitatively react with 6-aminomethylphthalhydrazide or 1,2-bis(phthalhydrazino) ethylenediamine in the presence of a weak oxidizing agent.

The resulting derivative emits strong luminescence when it is subject to the oxidative degradation with a proper oxidizing agent. Detecting the luminescence enables a quantitative analysis of 5-hydroxyindoles.

Likewise, as shown in FIG. 2 catecholamines approximately quantitatively react with 6-aminomethylphthalhydrazide or 1,2-bis(phthalhydrazino) ethylenediamine in the presence of a weak oxidizing agent.

The resulting derivative emits also strong luminescence when it is subject to the oxidative degradation with a proper oxidizing agent. Detecting that luminescence enables a quantitative analysis of catecholamines.

Furthermore, the inventors of the invention have found out that the above-mentioned derivative formation reaction progresses approximately quantitatively even if it uses a mixture of 5-hydroxyindoles, a mixture of catecholamines or a mixture thereof, and that a mixture of the above-mentioned derivatives can be stably separated into respective derivatives of each component using ordinary high performance liquid chromatography separation condition.

Accordingly, one can employ two types of embodiment for the method and the device for the analysis of the above-mentioned mixture. Namely, one is the method for the measurement chemiluminescence in which at first the above-mentioned sample including one or more components to be analyzed is separated by means of ordinary separation conditions, then each separated component is made to react with a chemiluminescent labeling agent of the invention to be converted to its derivative, and subsequently the resulting derivative is treated with an oxidizing agent, and the device therefor. Another one is the method for the measurement of chemiluminescence in which at first the above-mentioned sample including one or more components to be analyzed is made to react with a chemiluminescent labeling agent of the invention to form its derivative mixture, then the above-mentioned mixture of the derivatives is separated by means of ordinary separation conditions, and subsequently each separated derivative is treated with an oxidizing agent, and the device therefor.

A purpose of the invention is to provide a method for the analysis of 5-hydroxyindole and its analog or catecholamine and its analog by using the chemiluminescent labeling agent represented by the following formula:

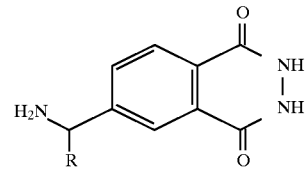

wherein R=H or

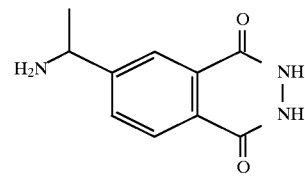

Another purpose of the invention is to provide a method for the analysis of 5-hydroxyindole and its analog or catecholamine and its analog, characterized in that above mentioned chemiluminescent labeling agent is reacted with 5-hydroxyindole and its analog or catecholamine and its analog to form its derivative, and luminescence emitted by oxidizing above mentioned derivatives is detected.

A further purpose of the invention is to provide a method for the analysis of 5-hydroxyindole and its analog or catecholamine and its analog, characterized in that above mentioned 5-hydroxyindole and its analog is at least one selected from the group consisting of 5-hydroxytryptophan, serotonin, 5-hydroxyindole-3-acetic acid, 5-hydroxyindole-3-acetamide, 5-hydroxytryptophol and N-acetylserotonin, or characterized in that above mentioned catecholamine and its analog is at least one selected from the group consisting of norepinephrine, epinephrine and dopamine.

A further purpose of the invention is to provide a method for the analysis of 5-hydroxyindole and its analog or catecholamine and its analog, characterized in that above mentioned derivatives based on said 5-hydroxyindole and its analog is the compound represented by the following formula:

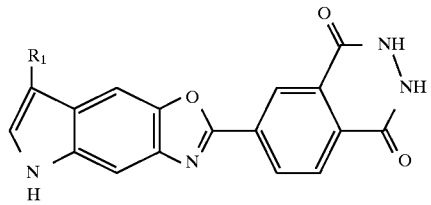

wherein $R_1$ represents $CH_2 CH_2 NH_2$, $CH_2 CH (CO_2 H) NH_2$, $CH_2 CO_2 H$, $CH_2 CONH_2$, $CH_2 CH_2 OH$ or $CH_2 CH_2 NHCOCH_3$, or characterized in that above mentioned derivative based on said catecholamine and its analog is the compound represented by the following formula:

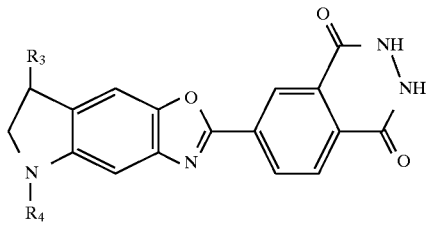

wherein $R_3$ represents H or OH, and $R_4$ represents H or $CH_3$.

A further purpose of the invention is to provide a method for the analysis of 5-hydroxyindole and its analog or catecholamine and its analog, characterized in that above mentioned oxidizing agent is at least one selected from the group consisting of hexacyanoferrate(III), hydrogen peroxide and peroxidase.

A yet another purpose of the inventions to provide a method for the analysis of 5-hydroxyindole and its analog and/or catecholamine and its analog mixture in a sample comprises;

a separation step of each component of 5-hydroxyindole and its analog and/or catecholamine, a derivative formation step of said separated each 5-hydroxyindole and its analog and/or catecholamine and its analog with a chemiluminescent labeling agent represented by the following formula:

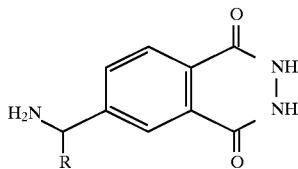

wherein R=H, or

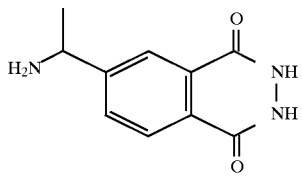

and a detection step of luminescence emitted by oxidizing above mentioned derivatives.

A further another purpose of the invention is to provide a device for the analysis of 5-hydroxyindole and its analog or catecholamine and its analog, characterized in that the device comprises;

a means of separating 5-hydroxyindole and its analog and/or catecholamine and its analog mixture in a sample, a means of forming the derivatives of above mentioned separated 5-hydroxyindole and its analog and/or catecholamine and its analog with a chemiluminescent labeling agent represented by the following formula:

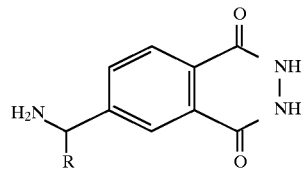

wherein R=H or

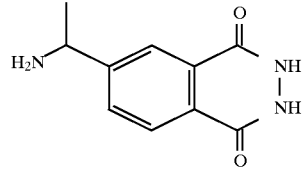

a means of making said derivative react with an oxidizing agent, and a means of detecting luminescence emitted by above mentioned reaction.

A another further purpose of the invention is to provide a device for the analysis of 5-hydroxyindols and catecholmines, characterized in that above mentioned 5-hydroxyindole and its analog is at least one selected from the group consisting of 5-hydroxytryptophan, serotonin, 5-hydroxyindole-3-acetamide, 5-hydroxytriptophol and N-acetylserotonin, or characterized in that said catecholamine and its analog is at least one selected from the group consisting of norepinephrine, epinephrine and dopamine.

A another further purpose of the invention is to provide a device for the analysis of 5-hydroxyindoles and catecholmines, characterized in that above mentioned derivatives based on said 5-hydroxyindole and its analog is the compound represented by the following formula:

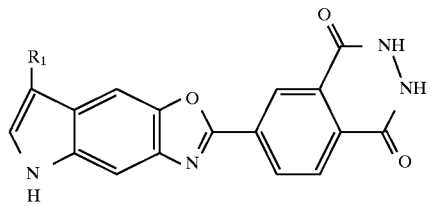

wherein $R_1$ represents $CH_2\ CH_2\ NH_2$, $CH_2\ CH\ (CO_2\ H)\ NH_2$, $CH_2\ CO_2\ H$, $CH_2\ CONH_2$, $CH_2\ CH_2\ OH$ or $CH_2\ CH_2\ NHCOCH_3$, or characterized in that said derivative based on said catecholamine and its analog is the compound represented by the following formula:

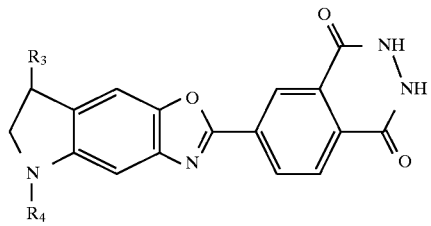

wherein $R_3$ represents H or OH, and $R_4$ represents H or $CH_3$.

A another further purpose of the invention is to provide a device for the analysis of 5-hydroxyindols and catecholmines, characterized in that said oxidizing agent is at least one selected from the group consisting of hexacyanoferrate(III), hydrogen peroxide and peroxidase.

A further purpose of the invention is to provide a device for the analysis of 5-hydroxyindole and its analog or catecholamine and its analog, characterized in that the device comprises;

a means of making the mixture of 5-hydroxyindole and its analog and/or catecholamine and its analog in a sample react with a chemiluminescent labeling agent represented by the following formula:

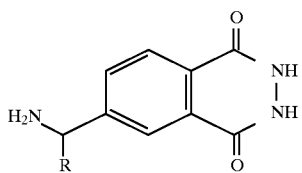

wherein R=H or

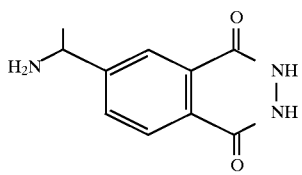

to form its derivative, a means of separating said derivative mixture, a means of making each said separated derivative to react with a oxidizing agent, and a means of detecting luminescence emitted by said reaction.

A further purpose of the invention is to pvide a device for the analysis of 5-hydroxyindole and its analog or catecholamine and its analog, characterized in that said 5-hydroxyindole and its analog is at least one selected from the group consisting of 5-hydroxytryptophan, serotonin, 5-hydroxyindole-3-acetic acid, 5-hydroxyindole-3-acetamide, 5-hydroxytriptophol and N-acetylserotonin, or characterized in that said catecholamine and its analog is at least one selected from the group consisting of norepinephrine, epinephrine and dopamine.

A yet another purpose of the invention is to provide a device for the analysis of 5-hydroxyindole and its analog or catecholamines ans analog, characterized in that above mentioned derivatives based on said 5-hydroxyindole and its analog is the compound represented by the following formula:

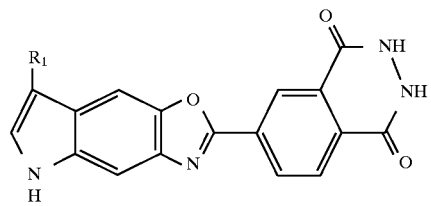

wherein $R_1$ represents $CH_2\ CH_2\ NH_2$, $CH_2\ CH\ (CO_2\ H)\ NH_2$, $CH_2\ CO_2\ H$, $CH_2\ CONH_2$, $CH_2\ CH_2\ OH$ or $CH_2\ CH_2\ NHCOCH_3$, or characterized in that said derivative based on said catecholamine and its analog is the compound represented by the following formula:

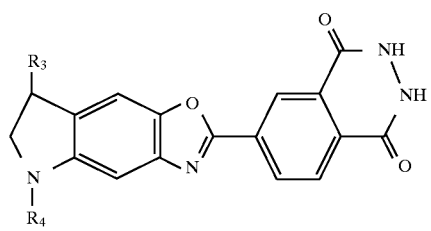

wherein $R_3$ represents H or OH, and $R_4$ represents H or $CH_3$.

A further purpose of the invention is to provide a device for the analysis of 5-hydroxyindole and its analog or catecholamines and its analog, characterized in that above mentioned oxidizing agent is at least one selected from the group consisting of hexacyanoferrate(III), hydrogen peroxide and peroxidase.

Explanation of Marks

1—HPLC system,
2—reaction coils,
3—6-aminomethylphthalhydrazide or 1,2-bis(phthalhydrazino)ethylenediamine, and a oxidizing agent mixture,
4—luminescence oxidizing agent,
5—chemiluminescence detector,
6—data processing device,
7—sample injector,
8—separation column,
9—eluate,
10—3-way joint

DESCRIPTION OF THE PREFERRED EMBODIMENT

Figure 1:
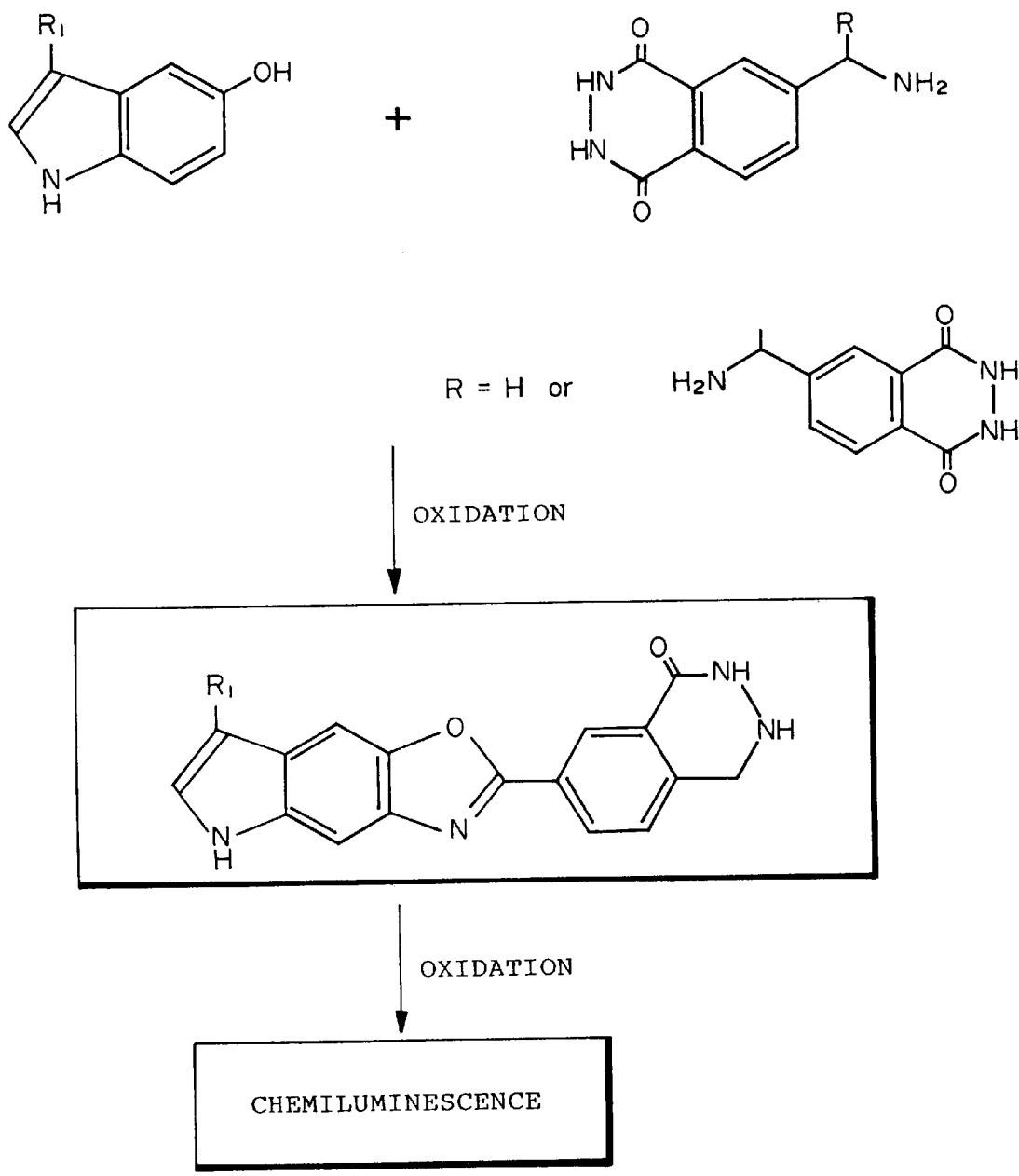
FIG. 1 shows a formation of a derivative in the reaction between 5-hydroxyindoles and 6-aminomethylphthalhydrazide or 1,2-bis(phthalhydrazino) ethylenediamine and the chemiluminescence by the oxidation of the above-mentioned derivative.
Figure 2:
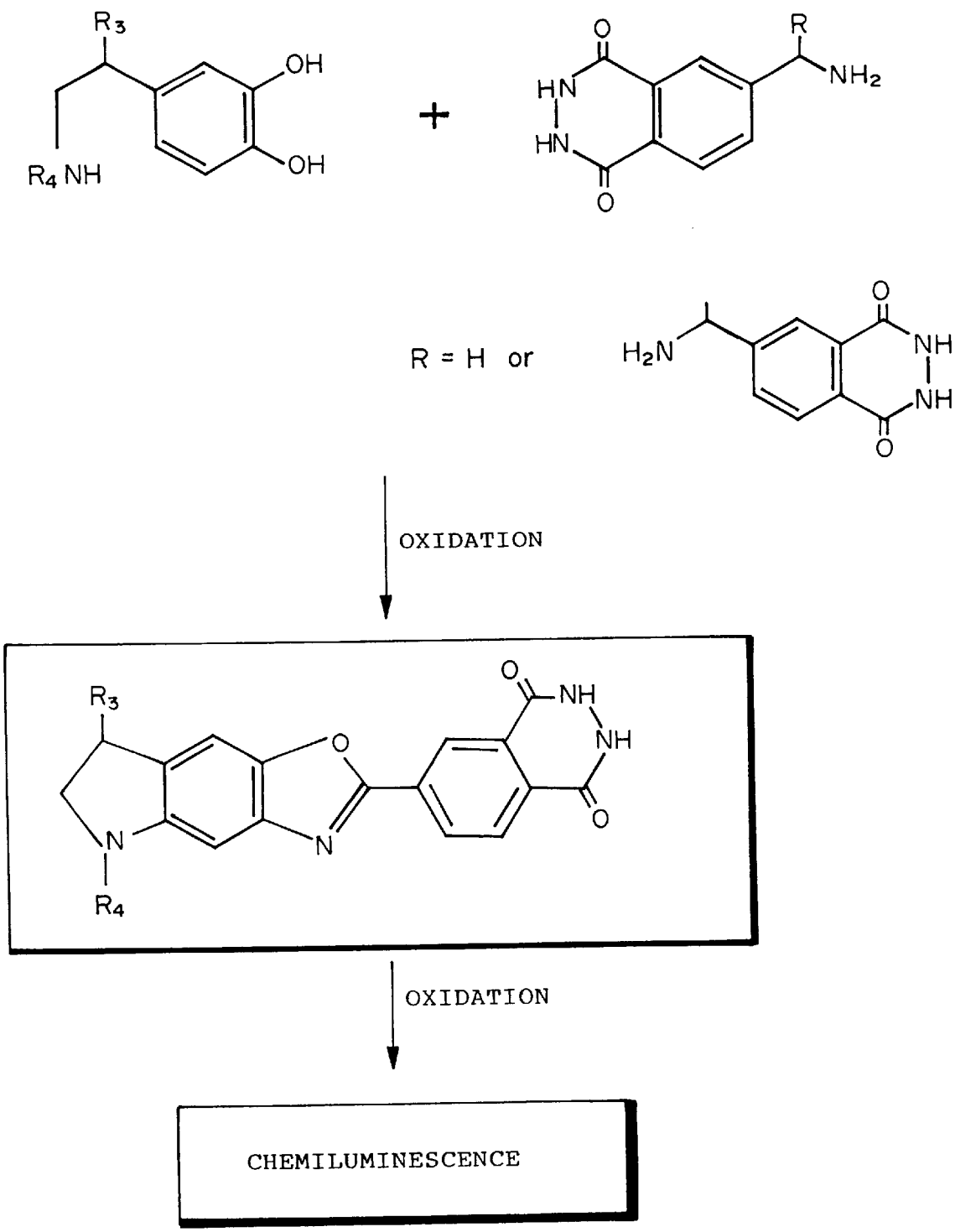
FIG. 2 shows a formation of a derivative in the reaction between catecholamines and 6-aminomethylphthalhydrazide and the chemiluminescence by the oxidation of the above-mentioned derivatives.
Figure 3:
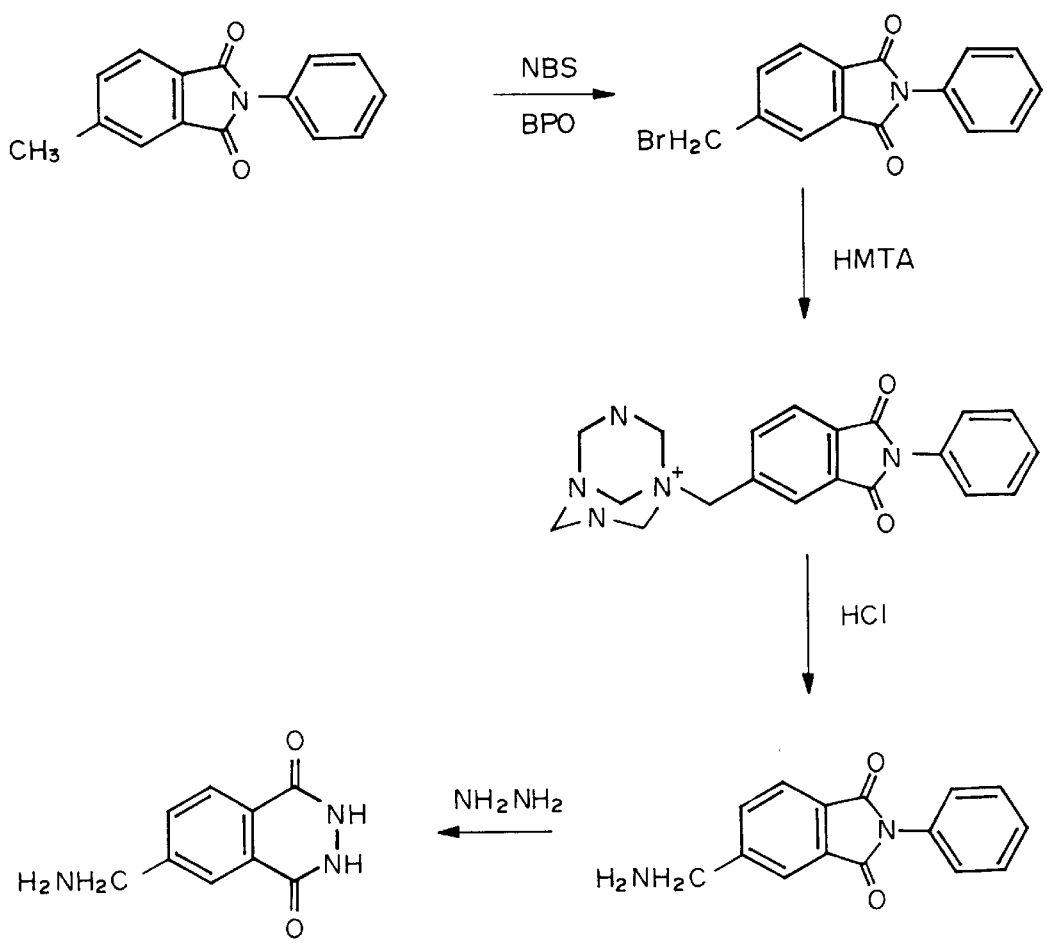
FIG. 3 shows a synthetic pathway of 6-aminomethylphthalhydrazide from 4-methyl-N-phenylphthalimide.

The invention will be explained further in detail in reference to some embodiments of the invention.
6-aminomethylphthalhydrazide
A method for synthesizing of 6-aminomethylphthalhydrazide as the derivativation reagent used in the invention is not particularly limited and for example, preferably it is synthesized in accordance with the reaction formula shown in FIG. 3. 4-methyl-N-phenylphthalimide is known as a starting material. Furthermore the bromination of its methyl group can be accomplished by an ordinary method in which it is reacted with N-bromosuccinimide(NBS) in the presence of a peroxide, such as benzoylperoxide(BPO). The method for conversion of the bromomethyl group of bromomethyl-N-phenylphthalimide to the aminomethyl group is not limited in the invention.

In the invention, it is particularly preferred that said group is reacted with hexamethylenetetramine to form its quaternary salt, the resulting salt is then isolated and subsequently the above-mentioned isolated salt is converted to aminomethyl group by Delepine reaction.

The resulting 4-aminomethyl-N-phenylphthalimide can be purified as white crystals not less than 95% of purity by recrystallization of its hydrochloride from the ethanol solution thereof. The structure of the purified one can be confirmed by a melting point, thin layer chromatography(TLC), liquid chromatography (HPLC), infrared absorption spectrum, nuclear magnetic resonance absorption spectrum and the like.

Furthermore, the method in which 4-aminomethyl-N-phenylphthalimide is neutralized and reacted with hydrazine to convert to 6-aminomethylphthalhydrazide is not particularly limited in the invention. In the invention, 6-aminomethylphthalhydrazide can be obtained in a high state of purity by preferably reacting with hydrazine in ethanol. In this invention, the purity of 6-aminomethylphthalhydrazide may be not less than 90%, preferably not less than 95%. It is most preferable to use it with not less than 99.5% of purity after using a method of recrystallization and the like, if necessary.

6-aminomethylphthalhydrazide are soluble in a water-miscible solvent, such as acetonitrile, ethanol, acetone, DMF, DMSO, and the resulting solution can be kept stable for the long term. In this invention, for example, where 6-aminomethylphthalhydrazide(not less than 95% of purity) is dissolved in water-acetonitrile (1:1 volume/volume) (concentration: about 10 mM), any substantial change in reactivity does not be observed after about one month.

1,2-bis(phthalhydrazino)ethylenediamine

Figure 4:
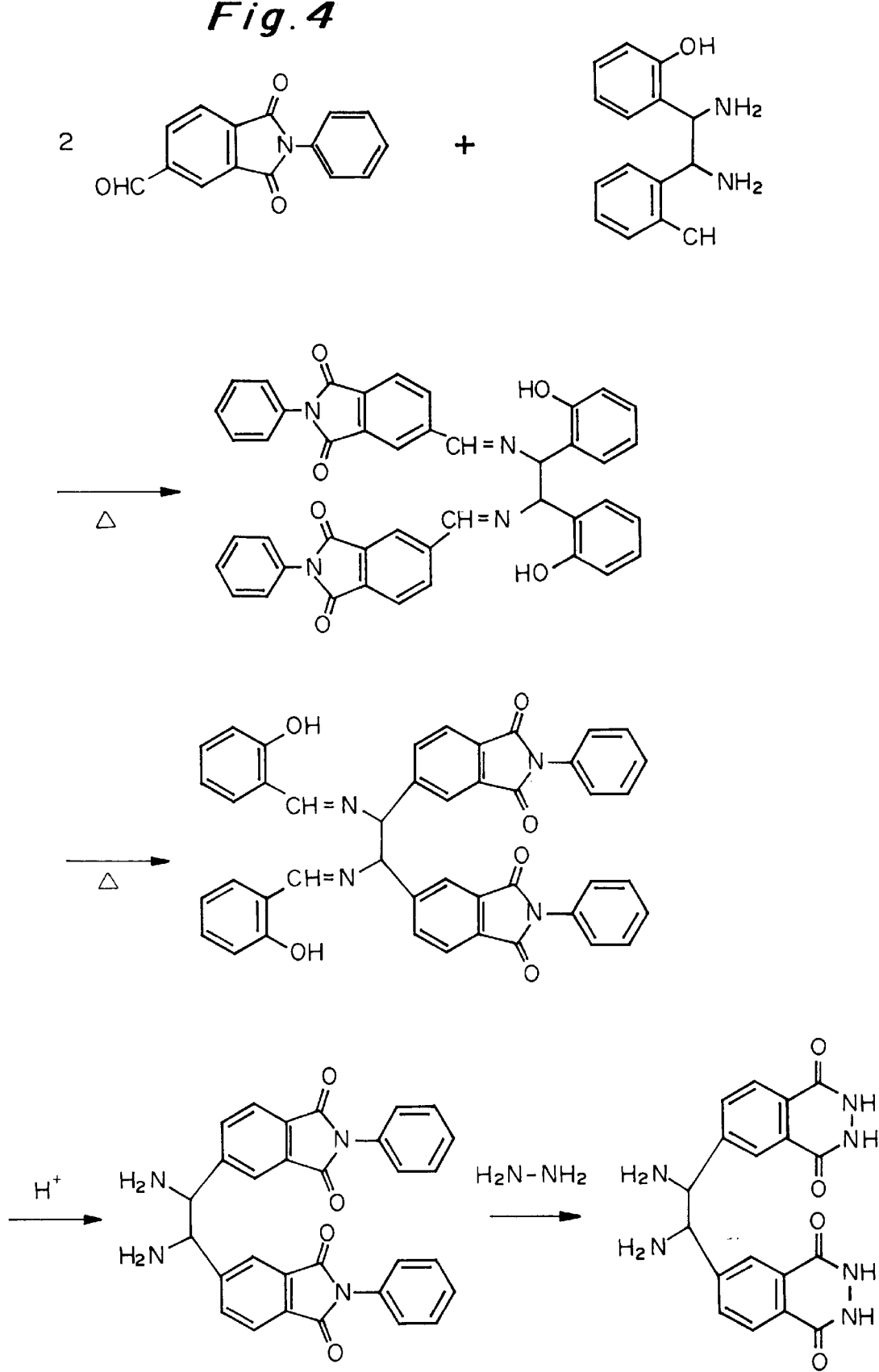
FIG. 4 shows a synthetic pathway of 1,2-bis(phthalhydrazino)ethylenediamine from 4-formyl-N-phenyl phthalimide and 1,2-bis(2-hydroxyphenyl)ethylenediamine.

The synthetic method of 1,2-bis(phthalhydrazino) ethylenediamine, as a new derivativation reagent used in the invention, is not particularly be limited. For example, preferably it can be synthesized in accordance with the synthetic pathway shown in FIG. 4. Namely, 1,2-bis(N-phenylphthalimide)ethylenediamine is obtained by the condensation reaction of between 1,2-bis(2-hydroxyphenyl) ethylenediamine (F. Vogetle, and oldschmit,Chem.Rev.,109, 1(1976)) and 4-formyl-N-phthalimide (J. Ishida, M. Takada, S. Hara, K. Sasamoto, K. Kina and M. Yamaguchi, Anal.Chim.Acta,309, 211–219(1995)) and by hydrolysis of the resulting Schiff base compound which is obtained by the rearrangement reaction. 1,2-bis(phthalhydrazino) ethylenediamine can be obtained by a further reaction with hydrazine. The purity of said reagent can be confirmed by a melting point, thin layer chromatography, liquid chromatography, infrared absorption spectrum, nuclear magnetic resonance absorption spectrum and the like.

In this invention, the purity of 1,2-bis(phthalhydrazino) ethylenediamine may be not less than 90%, preferably not less than 95%. It is most preferable to use it with not less than 99.5% of purity after recrystallization, and the like, if necessary.

1,2-bis(phthalhydrazino)ethylenediamine are soluble in a water-miscible solvent, such as acetonitrile, ethanol, acetone, DMF, DMSO, and the resulting solution can be kept stable for the long term. In this invention, for example, where 1,2-bis(phthalhydrazino)ethylenediamine (not less than 95% of purity) is dissolved in water-acetonitrile (1:1 volume/volume) (concentration: about 10 mM), any substantial change in reactivity does not be observed after about one month.

Reaction of 6-aminomethylphthalhydrazide with 5-hydroxyindoles

In this invention the reaction conditions for making 6-aminomethylphthalhydrazide react with 5-hydroxyindoles to form its derivatives is not particularly limited.

About 100 times equivalents of 6-aminomethylphthalhydrazide to 5-hydroxyindoles is preferably used.

A reaction solvent used in the invention is not particularly limited, but 5-hydroxyindoles or a mixture thereof as a sample is generally dissolved in any buffer, such as Bicine buffer, thus 6-aminomethylphthalhydrazide is preferably dissolved in a certain organic solvent which is miscible with those buffer. For example, acetonitrile, DMSO can be preferably used. A weak oxidizing agent which is added to the above-mentioned mixture is preferably used in a concentration of at least 1 mM.

A oxidizing agent which may be used in this invention is not particularly limited, and various organic oxidizing agents or inorganic oxidizing agents may be used. For example, various organic peroxides, such as peracetic acid, perbenzoic acid and alkylhydroperoxide may be preferably used as an organic oxidizing agent. Also various inorganic peroxides, such as hydrogen peroxides, sulfur peroxides, periodic acid and its salt and a metal oxidizing agent may be preferably used as a inorganic oxidizing agent. In this invention, particularly, hexacyanoferrate(III), such as potassium salt or sodium salt thereof may be preferably used as said oxidizing agent.

Furthermore, it is desirable that the formation of the derivative is completed by allowing to react the above-mentioned mixture at about 35°~45° C. Although the reaction time depends on the oxidizing agent and the like, it is preferably about 5~10 minutes. Furthermore, to reduce said reaction time, the reaction temperature is preferably up to 50° C.~100° C. For example, where 10 μl of hexacyanoferrate(III) (20 mM in water) is added to the mixture of serotonin (100 nM in Bicine buffer solution), as 5-hydroxyindoles, and 100 μl of 6-aminomethylphthalhydrazide (10 mM in acetonitrile) and is mixed at 30°~80° C., the derivative formation is completed within 2~10 minutes.

The resulting derivatives are stable in said solution, and it is not observed any substantial change in a concentration of 0.1~10 μM even after about 1 week.

The structure of said derivative can be confirmed by examining the yellow residues which is obtained by removing the solvent after the reaction, by using infrared absorption spectrum, nuclear magnetic resonance absorption spectrum, mass spectrometry method, thin layer chromatography and liquid chromatography and the like.

Furthermore in this invention, the preparation of the above-mentioned derivative may be done before 5-hydroxyindoles in a sample is separated by liquid chromatography and the like. In other words, a derivative mixture of each catechol component can be prepared by the above-mentioned derivativation reaction of 5-hydroxyindoles mixture in a sample, and then the resulting derivative mixture of each catechol component can be separated and subsequently the separated one can be subject to the after-mentioned luminescence reaction.

Alternatively, after 5-hydroxyindoles in a sample can be separated by liquid chromatography and the like, the separated each fraction can be subject to the above-mentioned derivativation and subsequently subject to the after-mentioned luminescent reaction. In this case, the required time for the derivativation can be controlled by selecting the reaction condition as discussed earlier.

Reaction of 1,2-bis(phthalhydrazino)ethylenediamine with 5-hydroxyindoles

In this invention the reaction conditions for making 1,2-bis(phthalhydrazino)ethylenediamine react with 5-hydroxyindoles to form its derivatives is not particularly limited.

About 100 times equivalents of 1,2-bis(phthalhydrazino)ethylenediamine to 5-hydroxyindoles is preferably used.

A reaction solvent used in the invention is not particularly limited, but 5-hydroxyindoles or a mixture thereof as a sample is generally dissolved in any buffer, such as Bicine buffer, thus 1,2-bis(phthalhydrazino)ethylenediamine is preferably dissolved in a certain organic solvent which is miscible with those buffer. For example, acetonitrile or DMSO can preferably be used.

A weak oxidizing agent which is added to the above-mentioned mixture is preferably used in a concentration of at least 1 mM.

A oxidizing agent which may be used in this invention is not particularly limited, various organic oxidizing agents or inorganic oxidizing agents may be used. For example, various organic peroxides, such as peracetic acid, perbenzoic acid and alkylhydroperoxide may be preferably used as an organic oxidizing agent. Also various inorganic peroxides, such as hydrogen peroxides, sulfur peroxides, periodic acid and its salt and a metal oxidizing agent may be preferably used as a inorganic oxidizing agent. In this invention, particularly, hexacyanoferrate(III), such as potassium salt or sodium salt thereof may be preferably used as said oxidizing agent.

Furthermore, it is desirable that the formation of the derivative is completed by allowing to react the above-mentioned mixture at about 35°~45° C. Although the reaction time depends on the oxidizing agent and the like, it is preferably about 5~10 minutes. Furthermore, to reduce said reaction time, the reaction temperature is preferably up to 50° C.~100° C. For example, where 10 $\mu$l of hexacyanoferrate(III) (20 mM in water) is added to the mixture of serotonin (100 nM in Bicine buffer solution), as 5-hydroxyindoles, and 100 $\mu$l of 1,2-bis(phthalhydrazino)ethylenediamine (10 mM in acetonitrile) and mixed at 30°~80° C., the derivative formation is completed within 2~10 minutes.

The resulting derivatives are stable in said solution, and it is not observed any substantial change in a concentration of 0.1~10 $\mu$M even after about 1 week.

The structure of said derivative can be confirmed by examining the yellow residues which is obtained by removing the solvent after the reaction, by using infrared absorption spectrum, nuclear magnetic resonance absorption spectrum, mass spectrometry method, thin layer chromatography and liquid chromatography and the like.

Furthermore, in this invention, the preparation of the above-mentioned derivative may be done before 5-hydroxyindoles in a sample is separated by liquid chromatography and the like. In other words, a derivative mixture of each 5-hydroxyindoles component can be prepared from 5-hydroxyindoles mixture in a sample by the above-mentioned derivativation reaction, and then the resulting derivative mixture of each 5-hydroxyindoles component can be separated and subsequently the separated one can be subject to the after-mentioned luminescence reaction.

Alternatively, after 5-hydroxyindoles in a sample can be separated by liquid chromatograph and the like, the separated each fraction can be subject to the above-mentioned derivativation and subsequently subject to the after-mentioned luminescent reaction. In this case, the required time for the derivativation can be controlled by selecting the reaction condition as discussed earlier.

As described above, the same derivative is obtained by making two kinds of chemiluminescent labeling agents of the invention to react with 5-hydroxyindoles. This is because that the derivative forming reaction is the oxidation reaction and the resulting derivative forms a benzoxazole ring and thereby it become stable. The structure of said derivative has a structure in which a phthalhydrazide group and a benzoxazole group are conjugated.

Chemiluminescence

In this invention at least 1~100 mM of the oxidizing agent preferably added to obtain sufficient chemiluminescence. Where said oxidizing agent is excess, the term of emitting luminescence is shorter than that of the measurement and thereby the efficient measurement is prevented.

A oxidizing agent which may be used in this invention is not particularly limited, and various organic oxidizing agents or inorganic oxidizing agents may be used. For example, various organic peroxides, such as peracetic acids and perbenzoic acids, alkylhydroperoxides may be preferably used as an organic oxidizing agent. Also various inorganic peroxides, such as hydrogen peroxides, sulfur peroxides, peroxidase, hemin and a metal oxidizing agent may be preferably used as a inorganic oxidizing agent. In this invention, particularly, hexacyanoferrate(III), such as potassium salt or sodium salt thereof may be preferably used as said oxidizing agent.

In this invention, chemiluminescence drived from said derivative exhibits its maximum at about 500 nm. Furthermore, mixed components other than the above-mentioned derivative, such as buffers, 5-hydroxyindoles, 6-methylaminophthalhydrazide, 1,2-bis(phthalhydrazino) ethylenediamine and an oxidation product, which had already emitted luminescence, do not emit chemiluminescence at all when they are reacted with the above-mentioned oxidizing agent. Accordingly, background noise is extremely low in this invention. Furthermore, 6-methylaminophthalhydrazide or 1,2-bis(phthalhydrazino) ethylenediamine does not react with sugars, keto acids, amino acids, nucleic acid bases, steroids, polyamines, carboxylic acids, alcohols or aldehydes to form a chemiluminescent compound at all.

Reaction rate of said chemiluminescence reaction is extremely fast, and for example, in the reaction of the serotonin derivative with 10 mM potassium hexacyanoferrate, the luminescence is emitted within 10 seconds after mixing.

Also, in the invention, the variation of a whole quantity of obtainable luminescence, which depends on a mixing method to be used, is a little.

Accordingly, in the invention, a detection device which may be used for the detection of said chemiluminescence is not particularly limited, and any device, which can detect the above-mentioned luminescence quantitatively, may be used. For example, one may preferably use any chemiluminescence measurement device, particularly any chemiluminescence detector combined with HPLC.

Luminescence mechanism

One may think that the reason of chemiluminescence in the invention is as follows. Said derivative has the specific structure which has phthalhydrazide group and benzoxazole group in the same molecular. By oxidative degradation of this derivative with a oxidizing agent, the formation of nitrogen from phthalhydrazide group leads to generate excess energy, and this energy is efficiently transferred to a benzoxazole group in the same molecule and excites it. Accordingly, the luminescence from excited benzoxazole group is assumed to be one of the source of chemiluminescence of the invention. Namely, as explained earlier, luminescence can be detected efficiently because there are one part which can generate and supply energy and another part which can be excited by receiving said energy and emit said excited energy as luminescence in the same molecule. This luminescence mechanism is assumed to differ from chemiluminescence, which is seen with luminol and the like, associated with oxidative degradation by only phthalhydrazide group.

Means of Separating

In this invention, means of separating 5-hydroxyindoles in a sample is not particularly limited. Ordinary high performance liquid chromatography can be used. ODS and the like, which is used in reverse phase system, can be preferably used as a packed material, and various types of buffer solution, such as acetonitrile, methanol or a mixture thereof and the like can be preferably used as a solvent. For example, the mixture of 5-hydroxytryptophan, serotonin, 5-hydroxyindole-3-acetic acid, 5-hydroxyindole-3-acetamide, 5-hydroxytriptophol, or N-acetyl serotonin (in Bicine buffer solution) can be separated by using ODS column packed material (for example, Shiseido-$C_{18}$ UG120 angstroms (5 μm, 4.6×250 mm)) and acetonitrile/acetate buffer solution (pH4) (volume ratio 1:4, 0.8 ml/min) as a solvent. In the above-mentioned condition, for example, each retention time ($t_R$ min) of 5-hydroxytryptophan, serotonin, 5-hydroxyindole-3-acetic acid, 5-hydroxyindole-3-acetamide, 5-hydroxytriptophol, or N-acetyl serotonin is about 10.3, 15.0, 17, 7.7, 21.3, 25.8, 32.6 minutes, respectively.

In the invention, means of separating catecholamines is not particularly limited. Ordinary high performance liquid chromatography can be used. A sample is usually dissolved in a buffer solution, thus ODS and the like, which is used in reverse phase system, can be preferably used as a packed material, and various types of buffer solution, such as acetonitrile, methanol or a mixture thereof and the like can be preferably used as a solvent. For example, in the separation of the mixture of norepinephrine, epinephrine and dopamine (in Bicine buffer solution), three kinds of catecholamine can be separated using ODS column packed material, and water or phosphate buffer solution and acetonitrile and the like as a solvent.

Derivativation reaction of 6-aminomethylphthalhydrazide with catecholamines

In this invention the reaction conditions for making 6-aminomethylphthalhydrazide react with catecholamines to form its derivatives is not particularly limited. About 100 times equivalents of 6-aminomethylphthalhydrazide to catecholamines is preferably used.

A reaction solvent used in the invention is not particularly limited, but catecholamines or a mixture thereof as a sample is generally dissolved in any buffer, such as Bicine buffer, thus 6-aminomethylphthalhydrazide is preferably dissolved in a certain organic solvent which is miscible with those buffer. For example, acetonitrile or DMSO can preferably be used.

A weak oxidizing agent which is added to the above-mentioned mixture is preferably used in a concentration of at least 1 mM.

A oxidizing agent which may be used in this invention is not particularly limited, various organic oxidizing agents or inorganic oxidizing agents may be used. For example, various organic peroxides, such as peracetic acid, perbenzoic acid and alkylhydroperoxide may be preferably used as an organic oxidizing agent. Also various inorganic peroxides, such as hydrogen peroxides, sulfur peroxides, periodic acid and its salt and a metal oxidizing agent may be preferably used as a inorganic oxidizing agent. In this invention, particularly, hexacyanoferrate(III), such as potassium salt or sodium salt thereof may be preferably used as said oxidizing agent.

Furthermore, it is desirable that the formation of the derivative is completed by allowing to stir and react the above-mentioned mixture at about 35°~45° C. Although the reaction time depends on the oxidizing agent and the like, it is preferably about 1~60 minutes. Furthermore, to reduce said reaction time, the reaction temperature is preferably up to 50° C.~100° C. For example, where 10 μl of hexacyanoferrate(III) (20 mM in water) is added to the mixture of norepinephrine (100 nM in Bicine buffer solution), as catecholamines, and 100 μl of 6-aminomethylphthalhydrazide (10 mM in acetonitrile) and mixed at 30°~80° C., the derivative formation is completed within 5~40 minutes.

The resulting derivatives are stable in said solution, and it is not observed any substantial change in a concentration of 0.1~10 μM even after about 1 week.

The structure of said derivative can be confirmed by examining the yellow residues which is obtained by removing that solvent after that reaction, using infrared absorption spectrum, nuclear magnetic resonance absorption spectrum, mass spectrometry method, thin layer chromatography and liquid chromatography and the like.

Furthermore in this invention, the preparation of the above-mentioned derivative may be done before catecholamines in a sample is separated by liquid chromatography and the like. In other words, a derivative mixture of each catechol component can be prepared by the above-mentioned derivativation reaction of catecholamines mixture in a sample, and then the resulting derivative mixture of each catechol component can be separated and subsequently the separated one can be subject to the after-mentioned luminescence reaction.

Alternatively, after catecholamines in a sample can be separated by liquid chromatograph and the like, the separated each fraction can be subject to the above-mentioned derivativation and subsequently subject to the after-mentioned luminescent reaction. In this case, the required time for the derivativation can be controlled by selecting the reaction condition as discussed earlier.

EXAMPLE

The invention will be explained further in detail with reference to the following Examples, but this invention shall not be limited to those as long as do not exceed the scope of the invention.

Example 1
(Synthesis of 6-aminomethylphthalhydrazide)

4-methyl-N-phenyl phthalimide (10 g, K. Sasamoto and Y. Ohkura, Chem.Pharm.Bull.,39(2), 411–416(1991); $^1$H-NMR(DMSO-$d^6$):2.5(CH3),7.2–7.8(aromatic)) was mixed with N-bromosuccinimide (NBS) (8.3 g) and benzoyl peroxide (BPO) (0.4 g) in carbon tetrachloride, and then bromomethylation was accomplished by refluxing for 4 hours.

Reaction solvent was removed and the resulting bromomethylated material was purified by using column chromatography(silica gel/benzene) (melting point 176°~178° C.). The structure of the resulting product was confirmed by using TLC (silica gel, benzene, Rf 0.16), infrared absorption spectrum (IR:KBr, 1720 cm$^{-1}$(C=O)), $^1$H, $^{13}$C-nuclear magnetic resonance spectrum ($^1$H-NMR (DMSO-d$_6$):4.6(BrCH$_2$),7.3–8.0(aromatic)).

Furthermore two nearly equal intensity peaks(M+H)$^+$ (316) and (M+H+2)$^+$(318) were confirmed by using mass spectrometry (JEOL JMS-D300, FAB high speed electron impact, by Nihon Denshi, same as hereinafter). Furthermore bromomethylated material (5 g) was reacted with hexamethylenetetramine (HMTA) (2.5 g) in chloroform (250 ml) for one day at room temperature to obtain a deposited quaternary salt. The crude product was purified as a needle white crystal (decomposition point 224°~227° C.) by recrystallization from ethanol. The structure of the resulting product was confirmed by using TLC (silica gel, 25% ammonia water-acetone (1:49) Rf 0.04), infrared absorption spectrum (IR:KBr, 1710 cm$^{-1}$(C=O)), $^1$H, $^{13}$C-nuclear magnetic resonance spectrum ($^1$H-NMR(DMSO-d$_6$):4.6(CH$_2$-HMTA), 5.1(HMTA-CH$_2$), 7.9–8.4(aromatic)). Furthermore a (M)$^+$(376) peak was confirmed by a mass spectrometry.

Furthermore 1 g of this salt was reacted in 250 ml of 5% hydrochloric acid-containing ethanol at 50° C. to do the conversion to an aminomethyl group. That reaction was approximately quantitatively (decomposition point 218°~221° C.). Furthermore the purity and structure of the resulting product were confirmed by using TLC (silica gel, acetone Rf 0.3), infrared absorption spectrum (IR:KBr, 1710 cm$^{-1}$(C=O),3150 cm$^{-1}$(NH2)) and $^1$H, $^{13}$C-nuclear magnetic resonance absorption spectrum ($^1$H-NMR(MeOH-d$_4$) :4.6(CH$_2$N),7.5–8.2(aromatic)). Furthermore a (M+H)$^+$ (253) peak was confirmed by mass spectrometry.

One ml of hydrazine was added to 0.5 g of the resulting aminomethylated hydrochloride in 60 ml of ethanol, and then it was refluxed for about 30 minutes. After removing ethanol, the rough purified product was recrystalized from its ethanol solution to obtain 6-aminomethylphthalhydrazide with not less than 90% of purity (melting point 256°~260° C.). The structure of the resulting product was confirmed by using infrared absorption spectrometry (IR:KBr, 1650 cm$^{-1}$ (C=O), 3000 and 2700 cm$^{-1}$(NH3$^+$)), $^1$H, $^{13}$C-nuclear magnetic resonance spectrum ($^1$H-NMR(DMSO-d$_6$):4.28 (CH$_2$N),7.9–8.4(aromatic)). Furthermore a (M+H)$^+$(192) peak was confirmed by mass spectrometry.

Example 2
(Synthesis of 1,2-bis(phthalhydrazino)ethylenediamine)

4-formyl-N-phenylphthalimide (5 g, J. Ishida, M. Takada, S. Hara, K. Sasamoto, K. Kina, and M. Yamaguchi, Anal.Chim.Acta, 309, 211–219(1995)) and 1,2-bis (hydroxyphenyl)ethylenediamine (2.4 g, F. Voegtle and E. Goldschmit, Chem. Ber.,109, 1–40(1976)) were refluxed in 100 ml of acetonitrile for about 12 hours to form Schiff base and then 1,3-sigmatropic rearrangement reaction was accomplished. The progress of the reaction was confirmed by using thin layer chromatograph (TLC, ODS,Methanol, Rf 0.75) and the like.

The structure of the resulting product was confirmed by IR(KBr, 1720 cm$^{-1}$(C=O), 1620 cm$^{-1}$(C=N)). Furthermore a (M+H)$^+$peak (711) was detected and confirmed by mass spectrometry (TOF-MS) (Shimadzu SEisakusho, MALDI VI, same hereinafter).

The resulting Shiff base compound was hydrolyzed in 2N sulfuric acid. The sulfate salt of diamine was then dispersed in 1 50 ml hot water followed by neutralization by 10 ml of 5N NaOH. The structure of the resulting product (m.p.231–235C) was confirmed by IR(KBr, 3480 cm$^{-1}$ (NH2), 1705 cm$^{-1}$(C=O)) and mass spectroscopy (M+H)$^+$ peaks (503) and (M+Na)$^+$, respectively.

This product, without further purification, was dissolved in ethanol and hydrazine was added thereto, and then it was refluxed about 5 hours to obtain phthalhydrazide compound. After removing the solvent, th residual was purified by recrystallization from ethanol. The structure of the resulting 1,2-bis(phthalhydrazino)ethylenediamine was confirmed by IR(KBr, around 3400 cm$^{-1}$(NH2), 3180 cm$^{-1}$(NH), 1650 cm$^{-1}$(C=O)), NMR(D$_2$O, 4.37(CH), 7.79–8.1(aromatic)) and further a (M+H)$^+$peaks (381) was detected and confirmed by mass spectrometry.

Example 3
(Quantitative analysis of serotonin or 5-hydroxyindole acetic acid with 6-aminomethylphthalhydrazide)

(1) Twenty $\mu$g of 5-hydroxyindoles was dissolve in 1 liter of Bicine buffer solution to prepare 100 nM of the solution.

(2) Nineteen mg of 6-aminomethylphthalhydrazide (not less than 95% of purity) was dissolved in 10 ml of acetonitrile to prepare about 10 mM of the solution.

(3) Sixty-six mg of potassium hexacyanoferrate (III) was dissolve in 10 ml of sodium carbonate solution (50 mM) to prepare 20 mM solution.

(4) One hundred $\mu$l of 5-hydroxyindoles solution of (1) and 10 $\mu$l of 6-aminomethylphthalhydrazide solution of (2) were mixed and 10 $\mu$l of potassium hexacyanoferrate(III) solution of (4) added thereto and then resulting mixture was reacted at about 37° C. for 10 minutes.

The completion of the derivative formation was confirmed by confirming approximately complete disappearance of 5-hydroxyindoles using HPLC (ODS reverse phase column; solvent:acetonitrile/phosphate buffer solution (1:4 volume/volume).

(5) The resulting reaction solution of (4) including the resulting derivative in question was transferred into a cell for detecting luminescence, and after which the cell was inserted into a luminescent measurement department (microleader MLR-100 by Corona).

(6) One hundred $\mu$l of potassium hexacyanoferrate(III) solution of (3) was added to and luminescence was measured.

From this result, the limit of detection (3S/N) of each 5-hydroxyindoles by the chemiluminescence method of the invention is estimated as several pM. This value is high sensitivity about 1000 and over times that of the natural fluorescence methods.

Example 4
(Quantitative analysis of serotonin or 5-hydroxyindole acetic acid with 1,2-bis(phthalhydrazino)ethylenediamine)

(1) Twenty $\mu$g of 5-hydroxyindoles was dissolve in 1 liter of Bicine buffer solution to prepare 100 nM of the solution.

(2) 38 mg of 1,2-bis(phthalhydrazino)ethylenediamine (not less than 95% of purity) was dissolved in 10 ml of the mixture of 5 mM of NaOand acetonitrile(1:1,vol/vol) to prepare about 10 mM of the solution.

(3) Sixty-six mg of potassium hexacyanoferrate (III) was dissolve in 10 ml of sodium carbonate solution (50 mM) to prepare 20 mM solution.

(4) One hundred $\mu$l of 5-hydroxyindoles solution of (1) and 10 $\mu$l of 1,2-bis(phthalhydrazino)ethylenediamine solution of (2) were mixed and 10 $\mu$l of potassium hexacyanoferrate(III) solution of (4) added thereto, and then the resulting mixture was reacted at about 37° C. for 10 minutes.

The completion of the derivative formation was confirmed by confirming approximately complete disappearance of 5-hydroxyindoles using HPLC (ODS reverse phase column; solvent :acetonitrile/phosphate buffer solution (1:4 volume/volume).

(5) The resulting reaction solution of (4) including the resulting derivative in question was transferred into a cell for detecting luminescence, and after which that cell was inserted into a luminescent measurement department( microleader MLR-100 by Corona).

(6) One hundred μl of potassium hexacyanoferrate(III) solution of (3) was added to and luminescence was measured.

From this result, the limit of detection (3S/N) of each 5-hydroxyindoles by the chemiluminescence method of the invention is estimated as several pM. This value is high sensitivity about 1000 and over times that of the natural fluorescence methods.

Example 5
(Analysis of 5-hydroxyindoles with 6-aminomethylphthalhydrazide)

Serotonin and 5-hydroxyindole acetic acid were dissolved in Bicine buffer solution so as to be 10 mM respectively, and a sample mixture for analysis was prepared.

Figure 5:
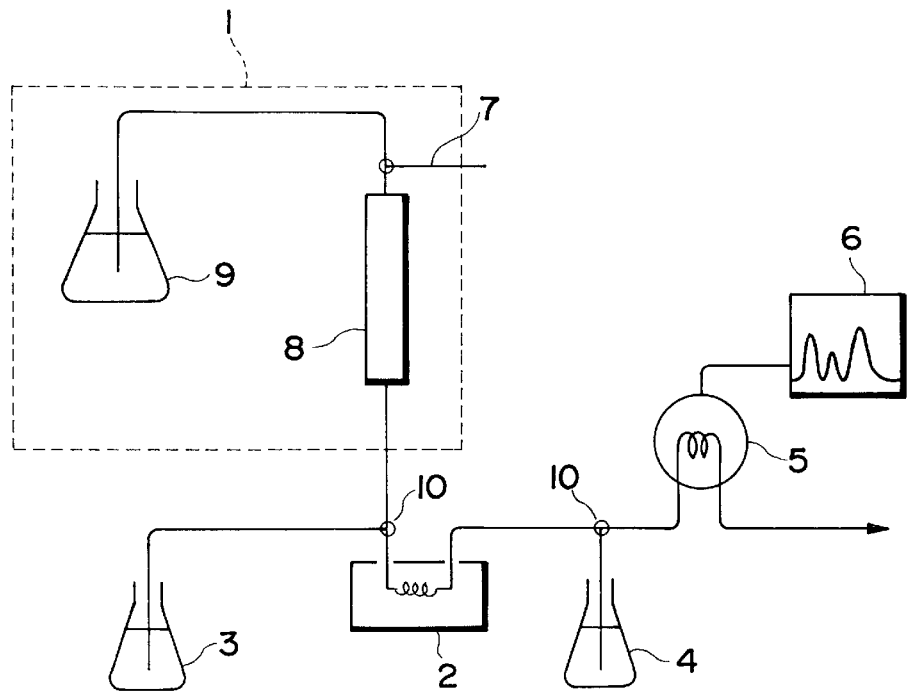
FIG. 5 shows a measurement system in which a sample mixture is separated by HPLC, subsequently subject to the derivativation and then measured.

(A) FIG. 5 shows one embodiment of means of measurement in which the resulting sample mixture is subject to the derivativation after separating. Namely, said means comprise a high performance liquid chromatograph (HPLC) system 1 for separating a sample mixture, a reaction coil 2 which mixes said separated each component with 6-aminomethylphthalhydrazide to form its derivative, a luminescence detector 5 which detects luminescence emitted when the resulting derivative is mixed with an oxidizing agent 4, and a data processing computer 6.

HPLC: LC10 by Shimazu Seisakusyo(Japan)

column:TSK-gel ODS80T$_M$, 150 mm eluate:mixture solvent of acetonitrile(10% volume) and citrate buffer solution (pH 3)(90% volume)

flow rate of the mobile phase: 0.8 ml/min.

reaction coil: 10 m of stainless steal tube (inner diameter, 0.5 mm)

reaction bath temperature: 80° C. 6-aminomethylphthalhydrazide:acetonitrile solvent(1 mM), which will be mixed by a peristaltic pump (0.8 ml/min.)

luminescence detector:chemiluminescence detector CLD10A by Shimazu Seisakusyo luminescence oxidizing agent:mixture of potassium hexacyanoferrate(III)(40 mM) and hydrogen peroxide (100 mM) (1 volume:1 volume), which will be mixed by a peristaltic pump (0.8 ml/min.)

After 100 μl of the sample mixture of (1) was introduced from sample injector 7 and separated with separation column 8 (the retention time of serotonin and 5-hydroxyindole acetic acid were about 8 and 13 minutes, respectively), 6-aminomethylphthalhydrazide solution was introduced into a mixing reaction coil through 3-way joint 10 and subject to a derivativation. Luminescence oxidizing agent 4 solution was introduced through 3-way joint 10 into luminescence mixing cell in company with the solution including a derivative, and emitting luminescence was detected.

The resulting luminescence was processed by the computer data processing device 6. In this way, serotonin and 5-hydroxyindole acetic acid emitted luminescence as single peak respectively, and the detection was completed in about 15 minutes.

By measuring a change of the quantity of luminescence depending on a concentration of each component and comparing with the standard curve which was made previously, it is found out that the limit of detection in S/N=3 is about 100 fg/injection volume, respectively.

Figure 6:
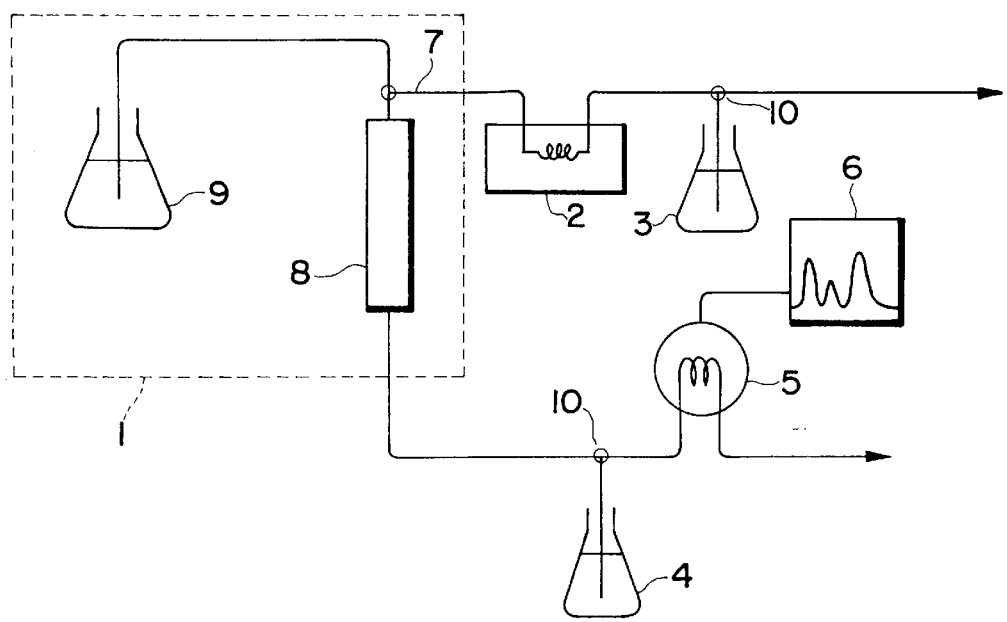
FIG. 6 shows a measurement system in which a sample mixture is subject to the derivativation, subsequently separated by HPLC and then measured.

(B) Also, FIG. 6 shows one embodiment of means of the measurement in which the resulting sample mixture is subject to the derivativation before separating. Namely, said means comprise a high performance liquid chromatograph (HPLC) system 1 for mixing the mixture, without being separated, with 6-aminomethylphthalhydrazide previously to form its derivative and separating the resulting derivative mixture, a luminescence detector 5 detects luminescence emitted when the separated derivative is mixed with an oxidizing agent 4, and a data processing computer 6.

HPLC: LC10 by Shimazu Seisakusyo(Japan)

column:Shiseido-C18UG120 angstrom(250 mm)

eluate:mixture solution of acetonitrile and phosphate buffer solution (1:1 volume/volume)

flow rate of the mobile phase: 0.8 ml/min.

luminescence detector:chemiluminescence detector CLD10A by Shimazu Seisakusyo luminescence oxidizing agent:mixture of potassium hexacyanoferrate(III)(40 mM) and hydrogen peroxide (100 mM) (1 volume:1 volume) in sodium carbonate solvent (50 mM), which will be mixed by a peristaltic pump (0.8 ml/min.)

One hundred μl of the sample mixture of (1) is mixed and reacted with 6-aminomethylphthalhydrazide solution to be subject to the derivativation. After the resulting derivative mixture is separated with a separation column( each retention time of serotonin and 5-hydroxyindole acetic acid were about 8 and 13 minutes, respectively), luminescence oxidizing agent solution 4 was introduced into a luminescence mixing cell through 3-way joint 10 in company with the solution including each derivative and emitting luminescence was detected.

The resulting luminescence was processed by the computer data processing device 6. In this way, serotonin and 5-hydroxyindole acetic acid emitted luminescence as single peak respectively, and the detection was completed in about 20 minutes.

By measuring a change of the quantity of luminescence depending on a concentration of each component and by comparing with the standard curve which was made previously, it is found out that the limit of detection in S/N=3 is about 100 fg/injection volume, respectively.

Example 6
(Analysis of 5-hydroxyindoles with 1,2-bis (phthalhydrazino)ethylenediamine)

Serotonin and 5-hydroxyindole acetic acid were dissolved in Bicine buffer solution so as to be 10 mM respectively, and a sample mixture for analysis was prepared.

(A) FIG. 5 shows one embodiment of means of measurement in which the resulting sample mixture is subject to the derivativation after separating. Namely, said means comprise a high performance liquid chromatograph (HPLC) system 1 for separating a sample mixture, a reaction coil 2 which mixes said separated each component with 1,2-bis (phthalhydrazino)ethylenediamine to form its derivative, a luminescence detector 5 which detects luminescence emitted when the resulting derivative is mixed with an oxidizing agent 4, and a data processing computer 6.

HPLC: LC10 by Shimazu Seisakusyo(Japan)

column:TSK-gel ODS80T$_M$, 150 mm eluate:mixture solvent of acetonitrile(10% volume) and citrate buffer solution (pH 3)(90% volume)

flow rate of the mobile phase: 0.8 ml/min.

reaction coil: 10 m of stainless steal tube (inner diameter, 0.5 mm)

reaction bath temperature: 80° C.

1,2-bis(phthalhydrazino)ethylenediamine:acetonitrile solvent(1 mM), which will be mixed by a peristaltic pump (0.8 ml/min.)

luminescence detector:chemiluminescence detector CLD10A by Shimazu Seisakusyo luminescence oxidizing agent:mixture of potassium hexacyanoferrate(III)(40 mM) and hydrogen peroxide (100 mM) (1 volume:1 volume), which will be mixed by a peristaltic pump (0.8 ml/min.)

After 100 μl of the sample mixture of (1) was introduced from sample injector 7 and separated with separation column 8 (the retention time of serotonin and 5-hydroxyindole acetic acid were about 8 and 13 minutes, respectively), 1,2-bis(phthalhydrazino)ethylenediamine solution was introduced into a mixing reaction coil through 3-way joint 10 and subject to a derivativation. Luminescence oxidizing agent 4 solution was introduced through 3-way joint 10 into luminescence mixing cell in company with the solution including a derivative, and emitting luminescence was detected.

The resulting luminescence was processed by the data processing computer device 6. In this way, serotonin and 5-hydroxyindole acetic acid emitted luminescence as single peak respectively, and the detection was completed in about 15 minutes.

By measuring a change of the quantity of luminescence depending on the concentration of each component and by comparing with the standard curve which was made previously, it is found out that the limit of detection in S/N=3 is about 100 fg/injection volume, respectively.

(B) Also, FIG. 6 shows one embodiment of means of the measurement in which the resulting sample mixture is subject to the derivativation before separating. Namely, said means comprise a high performance liquid chromatograph (HPLC) system 1 for mixing the mixture, without being separated, with 1,2-bis(phthalhydrazino)ethylenediamine previously to form its derivative and separating the resulting derivative mixture, a luminescence detector 5 which detects luminescent emitted when the separated derivative is mixed with an oxidizing agent 4, a and data processing computer 6.

HPLC: LC10 by Shimazu Seisakusyo(Japan)

column:Shiseido-C18UG120 angstrom(250 mm)

eluate:mixture solution of acetonitrile and phosphate buffer solution (1:1 volume/volume)

flow rate of the mobile phase: 0.8 ml/min.

luminescence detector:chemiluminescence detector CLD10A by Shimazu Seisakusyo luminescence oxidizing agent:mixture of potassium hexacyanoferrate(III)(40 mM) and hydrogen peroxide (100 mM) (1 volume:1 volume) in sodium carbonate solvent (50 mM), which will be mixed by a peristaltic pump (0.8 ml/min.)

One hundred μl of the sample mixture of (1) is mixed and reacted with 1,2-bis(phthalhydrazino)ethylenediamine solution to be subject to the derivativation. After the resulting derivative mixture is separated with a separation column( each retention time of serotonin and 5-hydroxyindole acetic acid were about 8 and 13 minutes, respectively), luminescence oxidizing agent solution 4 was introduced into a luminescence mixing cell through a switchable cock in company with the solution including each derivative and emitting luminescence was detected.

The resulting luminescence was processed by the computer data processing device 6. In this way, serotonin and 5-hydroxyindole acetic emitted luminescence as single peak respectively, and the detection was completed in about 20 minutes.

By measuring a change of the quantity of luminescence depending on the concentration of each component and by comparing with the standard curve which was made previously, it is found out that the limit of detection in S/N=3 is about 100 fg/injection volume, respectively.

Example 7
(Quantitative analysis of norepinephrine, epinephrine or dopamine)

(1) Twenty μg of catecholamine was dissolve in 1 liter of Bicine buffer solution to prepare 100 nM of the solution.

(2) Nineteen mg of 6-aminomethylphthalhydrazide (not less than 95% of purity) was dissolved in 10 ml of acetonitrile to prepare about 10 mM of the solution.

(3) Sixty-six mg of potassium hexacyanoferrate (III) was dissolve in 10 ml of sodium carbonate solution (50 mM) to prepare 20 mM solution.

(4) One hundred μl of catecholamine solution of (1) and 10 μl of 6-aminomethylphthalhydrazide solution of (2) were mixed and 10 μl of potassium hexacyanoferrate(III) solution of (4) added thereto and then the resulting mixture was reacted at about 37° C. for 10 minutes.

The completion of the derivative formation was confirmed by confirming approximately complete disappearance of catecholamine using HPLC (ODS reverse phase column; solvent:acetonitrile/phosphate buffer solution (1:4 volume/volume).

(5) The resulting reaction solution of (4) including the resulting derivative in question was transferred into a cell for detecting luminescence, and after which the cell was inserted into the luminescent measurement department( microleader MLR-100 by Corona).

(6) One hundred μl of potassium hexacyanoferrate(III) solution of (3) was added to and luminescence was measured.

From this result, the limit of detection (3S/N) of each catecholamine by the chemiluminescence method of the invention is estimated as several pM. This value is high sensitivity about 10 and over times that of the fluorescence method using 1,2-bis(phthalhydrazino)ethylenediamine.

Example 8
(Analysis of catecholamine mixture)

Norepinephrine, epinephrine and dopamine were dissolved in Bicine buffer solution so as to be 10 mM respectively, and a sample mixture for analysis was prepared.

(A) FIG. 5 shows one embodiment of means of the measurement in which the resulting sample mixture is subject to the derivativation after separating. Namely, said means comprise a high performance liquid chromatograph (HPLC) system 1 for separating a sample mixture, a reaction coil 2 which mixes said separated each component with 6-aminomethylphthalhydrazide to form its derivative, a luminescence detector 5 which detects luminescence emitted when the resulting derivative is mixed with an oxidizing agent 4, and a data processing computer 6.

HPLC: LC10 by Shimazu Seisakusyo(Japan)

column:TSK-gel ODS80T$^M$, 150 mm eluate:mixture solvent of acetonitrile(2% volume) and citrate buffer solution (pH 3)(98% volume)

flow rate of the moving phase: 0.8 ml/min.

reaction coil: 10 m of stainless steal tube (inner diameter, 0.5 mm)

reaction bath temperature: 80° C.

6-aminomethylphthalhydrazide:acetonitrile solvent(1 mM), which will be mixed by a peristaltic pump (0.8 ml/min.)

luminescence detector:chemiluminescence detector CLD10A by Shimazu Seisakusyo luminescence oxidizing agent:mixture of potassium hexacyanoferrate(III)(40 mM) and hydrogen peroxide (100 mM) (1 volume:1 volume), which will be mixed by a peristaltic pump (0.8 ml/min.)

After 100 μl of the sample mixture of (1) was introduced from sample injector 7 and separated with separation column 8 (the retention time of norepinephrine, epinephrine and dopamine were about 5, 8 and 12 minutes, respectively), 6-aminomethylphthalhydrazide solution was introduced into a mixing reaction coil through 3-way joint 10 and subject to the derivativation. Luminescence oxidizing agent 4 solution was introduced through 3-way joint 10 into luminescence mixing cell in company with the solution including the derivative, and emitting luminescence was detected.

The resulting luminescence was processed by the data processing computer device 6. In this way, norepinephrine, epinephrine and dopamine emitted luminescence as single peak respectively, and the detection was completed in about 15 minutes.

By measuring a change of the quantity of luminescence depending on a concentration of each component and by comparing with the standard curve which was made previously, it is found out that the limit of detection in S/N=3 is about 100 fg/injection volume, respectively.

(B) Also, FIG. 6 shows one embodiment of means of the measurement in which the resulting sample mixture is subject to the derivativation before separating. Namely, said means comprise a high performance liquid chromatograph (HPLC) system 1 for mixing the mixture, without being separated, with 1,2-bis(phthalhydrazino)ethylenediamine previously to form its derivative and separating the resulting derivative mixture, a luminescence detector 5 detects luminescent emitted when the separated derivative is mixed with an oxidizing agent 4, and a data processing computer 6.

HPLC: LC10 by Shimazu Seisakusyo(Japan)
column:TSK-gel ODS80T$_M$, 150 mm eluate:mixture solution of acetonitrile and phosphate buffer solution (1:1 volume/volume)

flow rate of the moving phase: 0.8 ml/min.

luminescence detector:chemiluminescence detector CLD10A by Shimazu Seisakusyo luminescence oxidizing agent:mixture of potassium hexacyanoferrate(III)(40 mM) and hydrogen peroxide (100 mM) (1 volume:1 volume) in sodium carbonate solvent (50 mM), which will be mixed by a peristaltic pump (0.8 ml/min.)

One hundred μl of the sample mixture of (1) is mixed and reacted with 6-aminomethylphthalhydrazide solution to be subject to the derivativation. After the resulting derivative mixture is separated with a separation column (each retention time of norepinephrine, epinephrine and dopamine were about 4, 7 and 10 minutes, respectively), luminescence oxidizing agent solution 4 was introduced into a luminescence mixing cell through 3-way joint 10 in company with the solution including each derivative and emitting luminescence was detected.

The resulting luminescence was processed by the computer data processing device 6. In this way, norepinephrine, epinephrine and dopamine emitted luminescence as single peak respectively, and the detection was completed in about 15 minutes.

By measuring a change of the quantity of luminescence depending on the concentration of each component and by comparing with the standard curve which was made previously, it is found out that the limit of detection in S/N=3 is about 100 fg/injection volume, respectively.

5-hydroxyindoles are reacted with 6-aminomethylphthalhydrazide or 1,2-bis(phthalhydrazino) ethylenediamine to form the same derivative. Furthermore, even if a mixture of 5-hydroxyindoles are used, the above-mentioned derivative is formed to produce a mixture containing each derivative.

When the above-mentioned derivative or the above-mentioned derivative mixture is oxidized, it emits strong chemiluminescence. This chemiluminescence has extremely low background noise when detecting luminescence, thus quantitative analysis of 5-hydroxyindoles with high sensitivity have became feasible. Similarly, catecholamines are reacted with 6-aminomethylphthalhydrazide to form the derivative. Furthermore, even if a mixture of catecholamines are used, the above-mentioned derivative is formed to produce a mixture containing each derivative. When the above-mentioned derivative or the above-mentioned derivative mixture is oxidized, it emits strong chemiluminescence. This chemiluminescence has extremely small background noise when detecting luminescence, thus quantitative analysis of catecholamines with high sensitivity have became feasible.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Applications No.149126/1995 filed on Jun. 15, 1995, No.156164/1995 filed on Jun. 22, 1995 and No.156177/1995 filed on Jun. 22, 1995 are hereby incorporated by reference.

What is claimed is:

1. A method for analyzing 5-hydroxyindoles and catecholamines, said method comprising the steps of:

reacting at least one member selected from the group consisting of 5-hydroxyindoles and catecholamines with at least one chemiluminescent labeling agent to form at least one derivative, said chemiluminescent labeling agent being selected from the group consisting of:

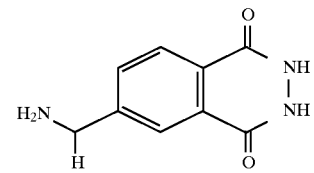

and

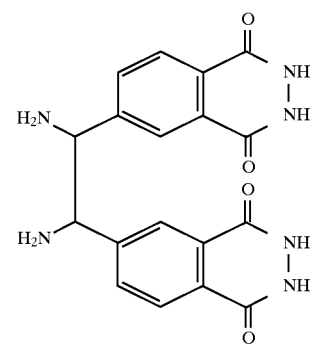

oxidizing said derivative, and detecting luminescence emitted by said step of oxidizing said derivative.

2. The method according to claim 11, wherein when said 5-hydroxyindoles include one or more members selected from the group consisting of 5-hydroxytryptophan, serotonin, 5-hydroxyindole-3-acetic acid, 5-hydroxyindole-3-acetamide, 5-hydroxytriptophol and N-acetylserotonin, and wherein said catecholamines include one or more members selected from the group consisting of norepinephrine, epinephrine and dopamine.

3. The method according to claim 2, wherein when said derivative is based on said 5-hydroxyindoles, said derivative is at least one compound represented by the following formula:

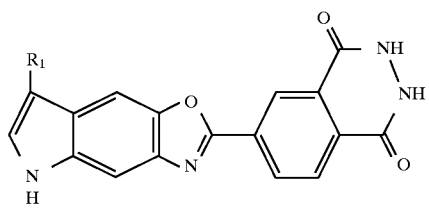

wherein $R_1$ represents $CH_2CH_2NH_2$, $CH_2CH(CO_2H)NH_2$, $CH_2CO_2H$, $CH_2CONH_2$, $CH_2CH_2OH$ or $CH_2CH_2NHCOCH_3$, and wherein when said derivative is based on said catecholamines, said derivative is at least one compound represented by the following formula:

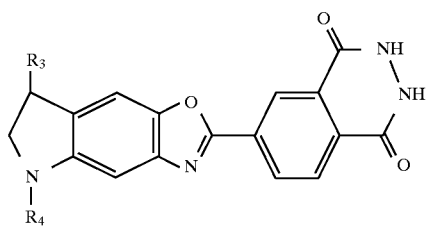

wherein $R_3$ represents H or OH, and $R_4$ represents H or $CH_3$.

4. The method according to claim 3, wherein said oxidizing step comprises oxidizing said derivative with at least one oxidizing agent, and further wherein said oxidizing agent is at least one member selected from the group consisting of hexacyanoferrate (III), hydrogen peroxide and peroxidase.

5. A method for analyzing a mixture comprising at least two members selected from the group consisting of 5-hydroxyindoles and catecholamines in a sample, said method comprising the steps of:

providing a mixture comprising at least two components selected from the group consisting of 5-hydroxyindoles and catecholamines and separating said components from each other to form separated components;

forming derivatives of said separated components with at least one chemiluminescent labeling agent; and oxidizing said derivatives and detecting luminescence emitted by said oxidizing step, wherein said chemiluminescent label agent is selected from the group consisting of:

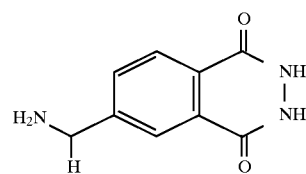

and

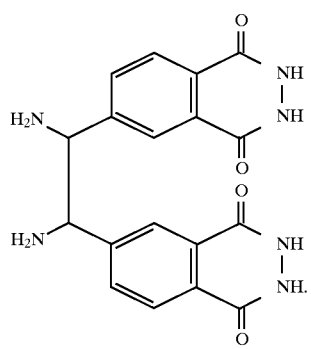

6. A device for the analysis of 5-hydroxyindoles and catecholamines, said device comprising:

means for separating a mixture comprising at least two components selected from the group consisting of 5-hydroxyindoles and catecholamines in a sample into separated components;

means for forming derivatives of said separated components with at least one chemiluminescent labeling agent;

means for making said derivatives react with at least one oxidizing agent; and means for detecting luminescence emitted by said reaction between said derivative and said oxidizing agent, wherein said chemiluminescent labeling agent is selected from the group consisting of:

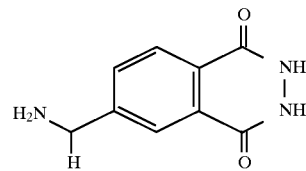

and

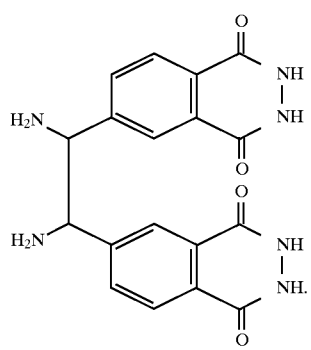

7. The device according to claim 6, wherein said 5-hydroxyindoles include one or more members selected from the group consisting of 5-hydroxytryptophan, serotonin, 5-hydroxyindole-3-acetic acid, 5-hydroxyindole- 3-acetamide, 5-hydroxytriptophol and N-acetylserotonin, and wherein said catecholamines include one or more members selected from the group consisting of norepinephrine, epinephrine and dopamine.

8. The device according to claim 7, wherein when one or more of said derivatives are based on said 5-hydroxyindoles, said derivatives based on said 5-hydroxyindoles are represented by the following formula:

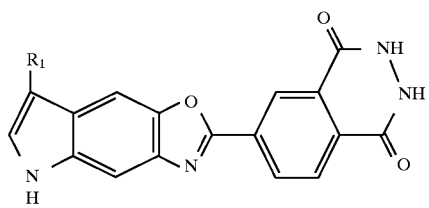

wherein $R_1$ represents $CH_2CH_2NH_2$, $CH_2CH(CO_2H)NH_2$, $CH_2CO_2H$, $CH_2CONH_2$, $CH_2CH_2OH$ or $CH_2CH_2NHCOCH_3$, and wherein when one or more of said derivatives are based on said catecholamines, said derivatives based on said catecholamines are represented by the following formula:

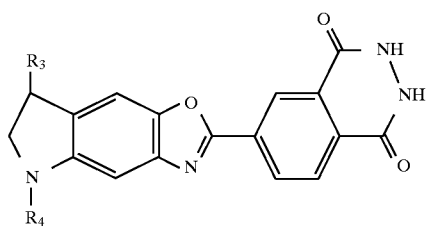

wherein $R_3$ represents H or OH, and $R_4$ represents H or $CH_3$.

9. The device according to claim 8, wherein said oxidizing agent is at least one member selected from the group consisting of hexacyanoferrate (III), hydrogen peroxide and peroxidase.

10. A device for the analysis of 5-hydroxyindoles and catecholamines, said device comprising:
   means for reacting a mixture comprising at least two components selected from the group consisting of 5-hydroxyindoles and catecholamines in a sample with at least one chemiluminescent labeling agent to form a mixture comprising derivatives of said components;
   means for separating said derivatives of said components into separated derivative components;
   means for making said separated derivative components react with at least one oxidizing agent; and
   means for detecting luminescence emitted by said reaction between said separated derivative components and said oxidizing agent,
   wherein said chemiluminescent labeling agent is selected from the group consisting of:

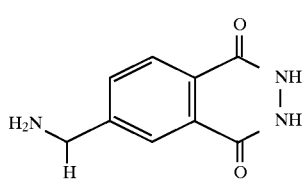

-continued
and

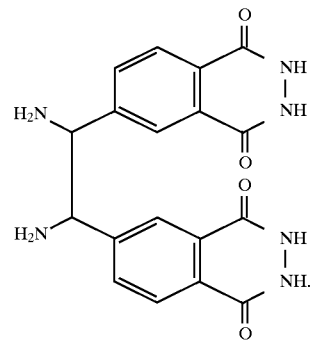

11. The device according to claim 10, wherein said 5-hydroxyindoles include one or more members selected from the group consisting of 5-hydroxytryptophan, serotonin, 5-hydroxyindole-3-acetic acid, 5-hydroxyindole-3-acetamide, 5-hydroxytriptophol and N-acetylserotonin, and wherein said catecholamines include one or more members selected from the group consisting of norepinephrine, epinephrine and dopamine.

12. The device according to claim 11, wherein when one or more of said derivatives of said components are based on said 5-hydroxyindoles, said derivative components based on said 5-hydroxyindoles are represented by the following formula:

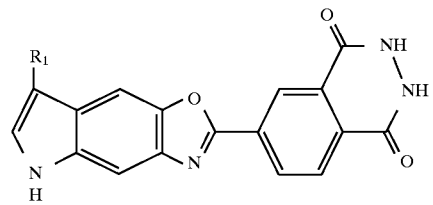

wherein $R_1$ represents $CH_2CH_2NH_2$, $CH_2CH(CO_2H)NH_2$, $CH_2CO_2H$, $CH_2CONH_2$, $CH_2CH_2OH$ or $CH_2CH_2NHCOCH_3$, and wherein when one or more of said derivative components are based on said catecholamines, said derivative components based on said catecholamines are represented by the following formula:

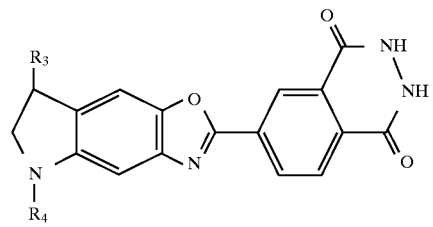

wherein $R_3$ represents H or OH, and $R_4$ represents H or $CH_3$.

13. The device according to claim 12, wherein said oxidizing agent is at least one member selected from the group consisting of hexacyanoferrate (III), hydrogen peroxide and peroxidase.

* * * * *